United States Patent
Lee et al.

(10) Patent No.: US 8,670,599 B2
(45) Date of Patent: Mar. 11, 2014

(54) FINGERPRINT AUTHENTICATION APPARATUS HAVING A PLURALITY OF FINGERPRINT SENSORS AND METHOD FOR SAME

(75) Inventors: Jea-Won Lee, Seongnam-si (KR); Bong-Seop Song, Seoul (KR); Young-Soo Moon, Seoul (KR); Ja-Sung Ku, Yongin-si (KR); Seong-Jik Lee, Yongin-si (KR); Dong-Mok Shin, Seongnam-si (KR)

(73) Assignee: SUPREMA Inc., Seongnam-si (KR)

( * ) Notice: Subject to any disclaimer, the term of this patent is extended or adjusted under 35 U.S.C. 154(b) by 168 days.

(21) Appl. No.: 13/338,932

(22) Filed: Dec. 28, 2011

(65) Prior Publication Data

US 2012/0098948 A1    Apr. 26, 2012

Related U.S. Application Data

(63) Continuation of application No. PCT/KR2010/004181, filed on Jun. 28, 2010.

(30) Foreign Application Priority Data

Jul. 1, 2009  (KR) .................. 10-2009-0059941

(51) Int. Cl.
*H04N 7/18* (2006.01)
(52) U.S. Cl.
USPC ............................................ 382/124; 348/77

(58) Field of Classification Search
USPC .............................................. 348/77; 382/124
See application file for complete search history.

(56) References Cited

U.S. PATENT DOCUMENTS

| 4,792,226 | A | * | 12/1988 | Fishbine et al. ................. 356/71 |
| 2002/0076089 | A1 | * | 6/2002 | Muramatsu et al. .......... 382/124 |
| 2004/0190761 | A1 | | 9/2004 | Lee |
| 2005/0169503 | A1 | * | 8/2005 | Howell et al. ................. 382/115 |
| 2005/0188213 | A1 | * | 8/2005 | Xu ................................ 713/186 |
| 2008/0187189 | A1 | | 8/2008 | Shin et al. |

FOREIGN PATENT DOCUMENTS

| EP | 1353291 A2 | * | 10/2003 |
| KR | 10-2002-0075886 | | 6/2004 |
| KR | 10-2008-0073054 A | | 8/2008 |
| KR | 10-0974815 | | 8/2010 |

* cited by examiner

*Primary Examiner* — Sath V Perungavoor
*Assistant Examiner* — Jeffery Williams
(74) *Attorney, Agent, or Firm* — NSIP Law

(57) ABSTRACT

A fingerprint authentication apparatus and method which processes fingerprint data input through a plurality of fingerprint sensors and uses the processed fingerprint data in authentication to thereby increase security and performance. The fingerprint authentication apparatus includes a first sensor configured to acquire first fingerprint data from a user; a second sensor configured to acquire second fingerprint data that is different from the first fingerprint data; and a control unit configured to determine whether or not to authenticate the user based on similarities obtained from the comparison of each of the first fingerprint data and the second fingerprint data with registered fingerprint data.

15 Claims, 3 Drawing Sheets

FINGERPRINT AUTHENTICATION APPARATUS HAVING A PLURALITY OF FINGERPRINT SENSORS AND METHOD FOR SAME

CROSS REFERENCE TO RELATED APPLICATION(S)

This application is a continuation of International Patent Application No. PCT/KR2010/004181, filed on Jun. 28, 2010, which claims the benefit of Korean Patent Application No. 10-2009-0059941 filed on Jul. 1, 2009, the entire disclosures of which are incorporated herein by reference for all purposes.

TECHNICAL FIELD

The present invention relates to user authentication, and more particularly, to fingerprint authentication which processes fingerprint data input through a plurality of fingerprint sensors and uses the processed fingerprint data in authentication to thereby increase security and performance.

BACKGROUND ART

There has been introduced a fingerprint authentication apparatus that includes a single fingerprint sensor to receive user's fingerprint data and authenticates a user by comparing the received user's fingerprint data with a previously registered fingerprint data.

In the case of use of a single fingerprint sensor, it is determined that a user is successfully authenticated when a calculation result of a similarity between input fingerprint data and previously registered fingerprint data is greater than a predefined threshold. That is, fingerprint data acquired by a variety of methods, for example, extracting feature points of a fingerprint using a fingerprint sensor, is compared to previously registered fingerprint data, and when the similarity therebetween is greater than, for example, 95%, it is determined that the user authentication is successful. In this case, the threshold is 0.95.

Hence, the authentication result may vary according to a threshold. For example, in a case in which a calculated similarity is 0.96, if a threshold is 0.95, it is determined that the user authentication is successful, whereas, if a threshold is 0.98, it is determined that the user authentication fails. In other words, a threshold defined too large may result in an authentication failure error even when a right user's fingerprint has been input. On the other hand, a threshold defined too small may result in an error of authenticating a wrong user with a wrong fingerprint. A rate of authentication failure with respect to a correct user fingerprint may be referred to as a false rejection rate (FRR), and a rate of false authentication for a wrong user fingerprint may be referred to as a false acceptance rate (FAR).

As such, since the single fingerprint sensor allows only one threshold to be used in authentication process, if the threshold is high, the FAR is lowered and the FRR is raised, and otherwise, if the threshold is low, the FAR is raised and the FRR is lowered. Thus, the performance of the fingerprint authentication apparatus and the occurrence of error may depend on a threshold.

Technical Problem

The objective of the present invention is to provide a fingerprint authentication apparatus and method which processes fingerprint data input through a plurality of fingerprint sensors according to a combined authentication algorithm and uses the processed data in authentication.

Technical Solution

The present invention provides a fingerprint authentication apparatus including: a first sensor configured to acquire first fingerprint data from a user; a second sensor configured to acquire second fingerprint data that is different from the first fingerprint data; and a control unit configured to determine whether or not to authenticate the user based on similarities obtained from the comparison of each of the first fingerprint data and the second fingerprint data with registered fingerprint data.

The control unit may be configured to determine whether or not to authenticate the user by further taking into consideration quality values of the acquired first and second fingerprint data. In addition, the control unit may be configured to determine whether or not to authenticate the user based on a combined score that is acquired by normalizing the sum of the product of a first score and a quality value of the first fingerprint data and the product of a second score and a quality value of the second fingerprint data wherein the first score is obtained from the similarity between the acquired first fingerprint data and the registered fingerprint data and the second score is obtained from the similarity between the acquired second fingerprint data and the registered fingerprint data.

Moreover, the control unit may be configured to calculate the combined score by further taking into consideration different weights that are assigned according to the importance of the first sensor and the second sensor.

The present invention also provides a fingerprint authentication method including: acquiring first fingerprint data and second fingerprint data that is different from the first fingerprint data from a user; and determining whether or not to authenticate the user based on similarities obtained from the comparison of each of the first fingerprint data and the second fingerprint data with registered fingerprint data.

Additional features of the invention will be set forth in the description which follows, and in part will be apparent from the description, or may be learned by practice of the invention.

Advantageous Effects

According to the present invention, it is possible to combine fingerprint data input through a plurality of fingerprint sensors and use the combined fingerprint data in authentication, and thus the false-rejection rate and the false-acceptance rate can be lowered, thereby obtaining a stable and accurate result of user authentication.

DESCRIPTION OF DRAWINGS

The accompanying drawings, which are included to provide a further understanding of the invention and are incorporated in and constitute a part of this specification, illustrate embodiments of the invention, and together with the description serve to explain the principles of the invention.

MODE FOR INVENTION

Figure 1:
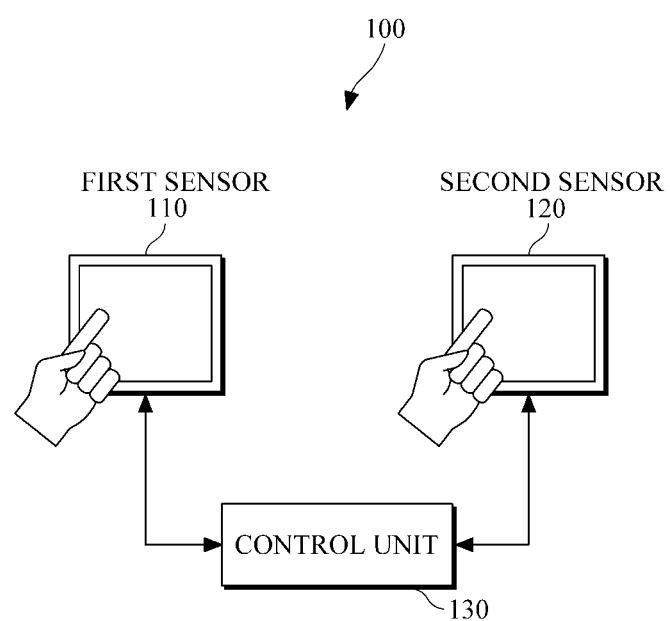
FIG. 1 is a diagram illustrating an example of a configuration of a fingerprint authentication apparatus according to an exemplary embodiment of the present invention.

The invention is described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

FIG. 1 is a diagram illustrating an example of a configuration of a fingerprint authentication apparatus according to an exemplary embodiment of the present invention.

Referring to FIG. 1, fingerprint authentication apparatus 100 may include a first sensor 110, a second sensor 120, and a control unit 130. The first sensor 110 and the second sensor 120 may be any types of fingerprint sensors, such as an optical sensor and a semiconductor sensor. In addition, the first sensor 110 and the second sensor 120 may be of the same type or different types.

A user may input one fingerprint through the first sensor 110 and input another fingerprint through the second sensor 120. The input of fingerprints may be performed sequentially or simultaneously. The control unit 130 may determine whether or not to authenticate the user based on a similarity resulting from the comparison of each of first fingerprint data acquired by the first sensor 110 and second fingerprint data acquired by the second sensor 120 with fingerprints previously registered therein. In addition, the first sensor 110 may receive a fingerprint of one user and the second sensor 120 may receive a fingerprint of another user.

According to the present embodiment, authentication may be performed by use of the two sensors through a variety of applications. As one example, only when the fingerprints of two users are simultaneously input and verified, it may be determined that user authentication is successfully performed.

In addition to the authentication by use of the combination of two sensors, the authentication may be performed through the two sensors which are used independently. For example, two sensors may be separately used for individual authentication of two users during busy time, for example at the time of clocking in or out at work or the like.

Moreover, one user may register a number of fingerprints through the sensors, and may follow an input order directed by the fingerprint authentication apparatus 100, for example, input order of "the index finger of the left hand" and "the third finger of the right hand." If the user inputs the fingerprints in the right order as directed, it is determined that the authentication is successful. If the two sensors are of different types, a sensor suitable for the user's state may be automatically selected for the user to register or authenticate the user's fingerprint. For example, if the user's fingers are dirty, one that is robust to contamination among the two sensors is automatically selected for use in authentication.

Hereinafter, a detailed algorithm for determining authentication will be described with reference to FIG. 2.

Figure 2:
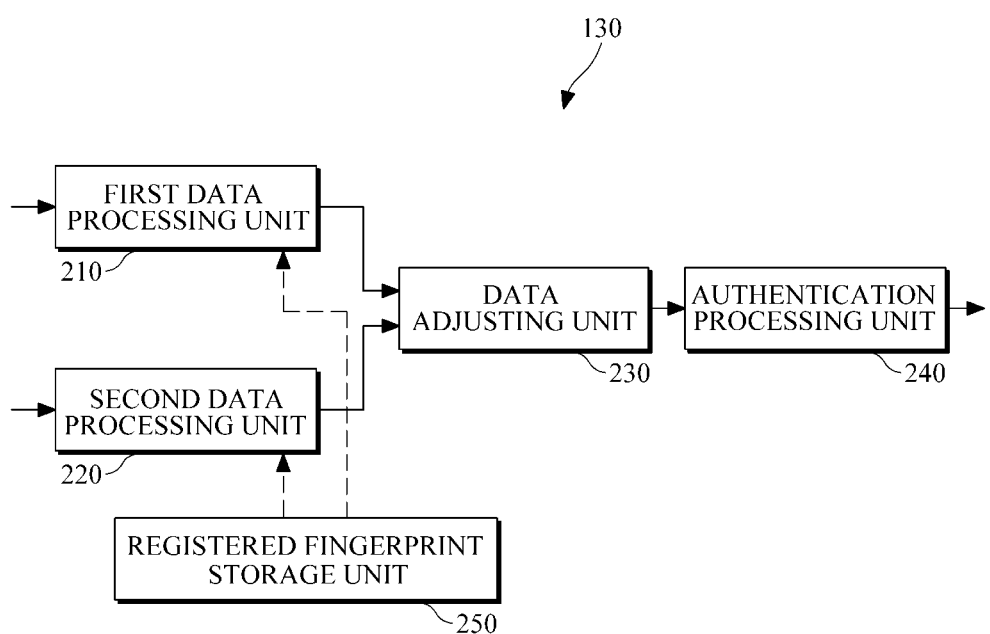
FIG. 2 is a diagram illustrating an example of a detailed configuration of a control unit 130 illustrated in FIG. 1.

FIG. 2 is a diagram illustrating an example of a detailed configuration of a control unit 130 illustrated in FIG. 1.

The control unit 130 may include a first data processing unit 210, a second data processing unit 220, a data adjusting unit 230, an authentication processing unit 240, and a registered fingerprint storage unit 250.

A similarity may be referred to as a score. The first data processing unit 210 may calculate a first score S1 that is a similarity between an input first fingerprint and one of registered fingerprints. In the same manner, the second data processing unit 220 may calculate a second score S2 that is a similarity between an input second fingerprint and one of the registered fingerprints. To calculate the similarity, data related to the registered fingerprints are read from the registered fingerprint storage unit 250. The registered fingerprint storage unit 250 may store pieces of data about the registered fingerprints of each registered users.

The first data processing unit 210 and the second data processing unit 220 may calculate a quality value of the input fingerprint data as well as the similarity of the input fingerprint data. The quality value is a measurement of a degree of quality of the input fingerprint with respect to the deterioration or sharpness of the input fingerprint, based on the number of feature points of a fingerprint used in calculating the similarity or the number of the feature points detected in a unit area. For example, fingerprint authentication can be performed by calculating a similarity based on a part of an input fingerprint which is contaminated, but it is appreciated that the quality of the fingerprint measured based on the part of the fingerprint is lower than a quality measured based on the similarity between the entire fingerprints. The example illustrated in FIG. 2 assumes that a quality value of the first fingerprint data is Q1 and a quality value of the second fingerprint data is Q2.

The data adjusting unit 230 may calculate a combined score SF for use in more accurate authentication. The combined score SF may be, for example, (Q1×S1+Q2×S2), or (Q1×S1+Q2×S2)/(Q1+Q2) acquired by normalizing (Q1×S1+Q2×S2).

The authentication processing unit 240 may determine whether the authentication is successful based on the first score S1, the second score S2, and the combined score SF. More specifically, the success in the authentication may be determined according to an algorithm as below. Here, the algorithm uses 4 thresholds TL, TH, TM and TF wherein TH>TM>TL.

```
IF( S1 < TL or S2 < TL ) Fail
ELSE IF( S1 >= TH or S2 >= TH ) Succeed
ELSE IF( S1 >= TM or S2 >= TM ) {
   IF( SF >= TF ) Succeed
   ELSE Fail
}
ELSE Fail
```

More specifically, if either the first score S1 or the second score S2 is smaller than the threshold TL, it indicates that there is an unlike input fingerprint, and thus it is determined that the authentication fails, whereas if either the first score S1 or the second score S2 is equal to or greater than the threshold TH, it is determined that the authentication is successful. In addition, if both the first score S1 and the second score S2 are smaller than the threshold TH or if either the first score S1 or the second score S2 is smaller than the threshold TH but equal to or greater than the threshold TM which is greater than TL, it is determined that the authentication is successful when the combined score SF is equal to or greater than the threshold TF.

In the case in which the first sensor 110 and the second sensor 120 are of different types, the combined score SF may be calculated by taking into consideration different weights that are assigned according to the importance of each sensor. For example, if the first sensor 110 is an optical sensor and the second sensor 120 is a semiconductor sensor, in assigning different weights W1 and W2 to the respective first and second sensors 110 and 120, recognition results of the first sensor 110 and the second sensor 120 may be taken into consideration. In this case, the combined score SF may be calculated as (W1×Q1×S1+W2×Q2×S2) or as (W1×Q1×S1+W2×Q2×S2)/(W1×Q1+W2×Q2) obtained by normalizing (W1×Q1×S1+W2×Q2×S2).

Figure 3:
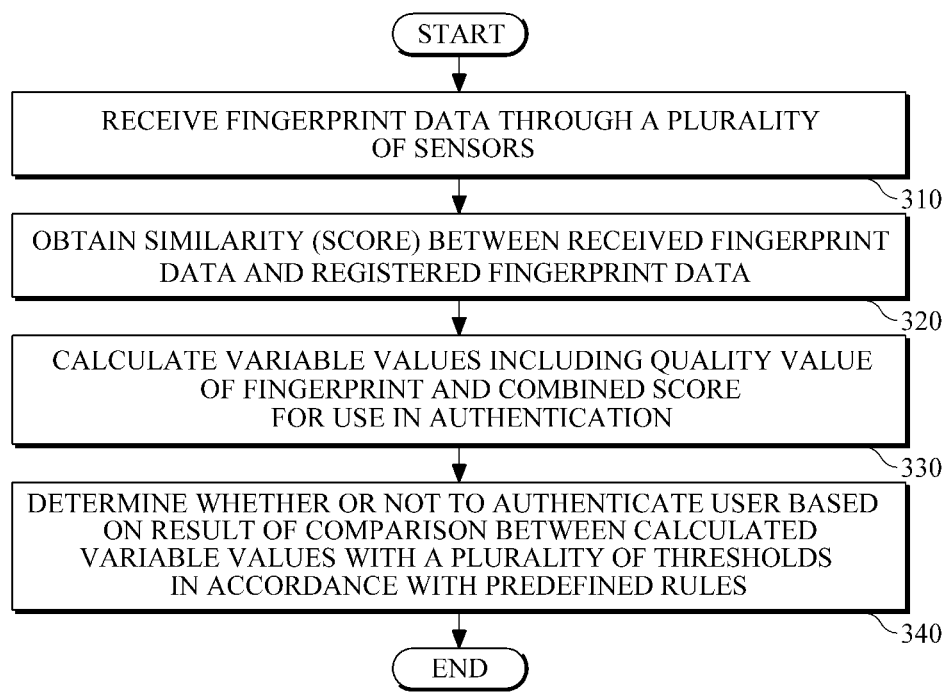
FIG. 3 is a flowchart illustrating an example of a fingerprint authentication method according to an exemplary embodiment of the present invention.

FIG. 3 is a flowchart illustrating an example of a fingerprint authentication method according to an exemplary embodiment of the present invention.

Fingerprint data is received from each of a plurality of sensors (310). Similarities, that is, a first score S1 and a second score S2, are obtained from the comparison of the input fingerprint data and registered fingerprint data (320). As described above, the sensors receive data about different fingerprints. As described with reference to FIG. 2, the quality value of the fingerprint is calculated and the data adjusting unit calculates a combined score SF (330). It is determined whether or not to authenticate the user based on the calculated combined score SF, the first score S1, and the second score S2 (340). As described above, the calculation of the combined score SF may be performed based on the quality value Q1 of the first fingerprint data and the quality value Q2 of the second fingerprint data in addition to the first score S1 and the second score S2. Moreover, the combined score SF may be calculated in consideration of different weights W1 and W2 that are assigned according to the importance of each of the first sensor 110 and the second sensor 120.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

INDUSTRIAL APPLICABILITY

The present invention can be efficiently applied to a security system equipped with a plurality of fingerprint sensors.

The invention claimed is:

1. A fingerprint authentication apparatus comprising:
a first sensor configured to acquire first fingerprint data from a user;
a second sensor configured to acquire second fingerprint data that is different from the first fingerprint data; and
a control unit configured to determine whether or not to authenticate the user based on similarities obtained from the comparison of each of the first fingerprint data and the second fingerprint data with registered fingerprint data, wherein the control unit is configured to determine whether or not to authenticate the user based on a combined score that is acquired by normalizing the sum of the product of a first score and a quality value of the first fingerprint data and the product of a second score and a quality value of the second fingerprint data wherein the first score is obtained from the similarity between the acquired first fingerprint data and the registered fingerprint data and the second score is obtained from the similarity between the acquired second fingerprint data and the registered fingerprint data.

2. The fingerprint authentication apparatus of claim 1, wherein the control unit is configured to determine that authentication is successful when either a first score or a second score is equal to or greater than a first threshold wherein the first score is obtained from the similarity between the acquired first fingerprint data and the registered fingerprint data and the second score is obtained from the similarity between the acquired second fingerprint data and the registered fingerprint data.

3. The fingerprint authentication apparatus of claim 1, wherein the control unit is configured to determine whether or not to authenticate the user by further taking into consideration quality values of the acquired first and second fingerprint data.

4. The fingerprint authentication apparatus of claim 1, wherein if both the first score and the second score are smaller than the first threshold or if either the first score or the second score is equal to or greater than a second threshold that is smaller than the first threshold, the control unit is configured to determine that authentication is successful when the combined score is equal to or a greater than a predetermined value.

5. The fingerprint authentication apparatus of claim 1, wherein the control unit is configured to calculate the combined score by further taking into consideration different weights that are assigned according to the importance of the first sensor and the second sensor.

6. The fingerprint authentication apparatus of claim 1, wherein the control unit is configured to determine that authentication is successful when fingerprints touched on both the first sensor and the second sensor are successfully verified.

7. The fingerprint authentication apparatus of claim 1, wherein the control unit is configured to control the first sensor and the second sensor to operate independently from each other so as to perform authentication in parallel or to select one of the first and the second sensors according to a user's characteristic so as to perform authentication.

8. The fingerprint authentication apparatus of claim 1, wherein the control unit is configured to instruct the user which finger to be used for authentication and the user touches the finger on one of the first and the second sensors in response to the instruction so as to perform fingerprint authentication.

9. A fingerprint authentication method comprising:
acquiring first fingerprint data and second fingerprint data that is different from the first fingerprint data from a user; and
determining whether or not to authenticate the user based on similarities obtained from the comparison of each of the first fingerprint data and the second fingerprint data with registered fingerprint data, wherein the determining of whether or not to authenticate the user comprises:
calculating a combined score by normalizing the sum of the product of a first score and a quality value of the first fingerprint data and the product of a second score and a quality value of the second fingerprint data wherein the first score is obtained from the similarity between the acquired first fingerprint data and the registered fingerprint data and the second score is obtained from the similarity between the acquired second fingerprint data and the registered fingerprint data, and,
if both the first score and the second score are smaller than the first threshold or if either the first score or the second score is equal to or greater than a second threshold that is smaller than the first threshold, determining that authentication is successful when the combined score is equal to or a greater than a predetermined value.

10. The fingerprint authentication method of claim 9, wherein the determining of whether or not to authenticate the user comprises further taking into consideration quality values of the acquired first and the second fingerprint data in addition to the similarities.

11. The fingerprint authentication method of claim 9, wherein the calculating of the combined score comprises taking into consideration different weights that are assigned according to the importance of the first sensor and the second sensor.

12. The fingerprint authentication method of claim 9, wherein the determining of whether or not to authenticate the user comprises determining that authentication is successful when fingerprints touched on both the first sensor and the second sensor are successfully verified.

13. The fingerprint authentication method of claim 9, wherein the determining of whether or not to authenticate the user comprises operating the first sensor and the second sensor independently from each other so as to perform authentication in parallel or selecting one of the first and the second sensors according to a user's characteristic so as to perform authentication.

14. The fingerprint authentication method of claim 9, wherein the determining of whether or not to authenticate the user comprises instructing the user which finger to be used for authentication and the user touches the finger on one of the first and the second sensors in response to the instruction so as to perform fingerprint authentication.

15. The fingerprint authentication apparatus of claim 4, wherein the control unit is configured to calculate the combined score by further taking into consideration different weights that are assigned according to the importance of the first sensor and the second sensor.

* * * * *